(12) United States Patent
Yoon et al.

(10) Patent No.: US 10,435,296 B2
(45) Date of Patent: Oct. 8, 2019

(54) LIQUID HYDROGEN STORAGE MATERIAL AND METHOD OF STORING HYDROGEN USING THE SAME

(71) Applicant: KOREA INSTITUTE OF SCIENCE AND TECHNOLOGY, Seoul (KR)

(72) Inventors: Chang Won Yoon, Seoul (KR); Dajung Han, Seoul (KR); Yeong Cheon Kim, Seoul (KR); Hyun Seo Park, Seoul (KR); Hyung Chul Ham, Seoul (KR); Sung Pil Yoon, Seoul (KR); Jonghee Han, Seoul (KR); Tae Hoon Lim, Seoul (KR); Suk Woo Nam, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 267 days.

(21) Appl. No.: 15/713,698

(22) Filed: Sep. 25, 2017

(65) Prior Publication Data
US 2018/0093889 A1 Apr. 5, 2018

(30) Foreign Application Priority Data

Sep. 30, 2016 (KR) .......................... 10-2016-0126557

(51) Int. Cl.
*C01B 3/00* (2006.01)
*C01B 3/54* (2006.01)
(Continued)

(52) U.S. Cl.
CPC ................. *C01B 3/54* (2013.01); *B01J 21/04* (2013.01); *B01J 23/44* (2013.01); *B01J 23/462* (2013.01);
(Continued)

(58) Field of Classification Search
None
See application file for complete search history.

(56) References Cited

U.S. PATENT DOCUMENTS 6,074,447 A * 6/2000 Jensen ..................... B01J 3/008
423/658.2
7,351,395 B1 * 4/2008 Pez ........................ C01B 3/0015
206/0.7
(Continued)

FOREIGN PATENT DOCUMENTS

JP 10194701 A 7/1998
JP 2002274801 A 9/2002
(Continued)

OTHER PUBLICATIONS

Katharina Stark et al., "Melting Points of Potential Liquid Organic Hydrogen Carrier Systems Consisting of N-Alkylcarbazoles", Journal of Chemical & Engineering Data, Mar. 17, 2016, pp. 1441-1448, vol. 61, American Chemical Society.
(Continued)

*Primary Examiner* — Wayne A Langel
(74) *Attorney, Agent, or Firm* — Cantor Colburn LLP

(57) ABSTRACT

Provided is a liquid hydrogen storage material including 1,1'-biphenyl and 1,1'-methylenedibenzene, the liquid hydrogen storage material including the corresponding 1,1'-biphenyl and 1,1'-methylenedibenzene at a weight ratio of 1:1 to 1:2.5. The corresponding liquid hydrogen storage material has excellent hydrogen storage capacity value by including materials having high hydrogen storage capacity, and is supplied in a liquid state, and as a result, it is possible to minimize initial investment costs and the like required when the corresponding liquid hydrogen storage material is used as a hydrogen storage material in a variety of industries.

13 Claims, 17 Drawing Sheets

(51) Int. Cl.
| | |
|---|---|
| C07C 15/16 | (2006.01) |
| B01J 23/44 | (2006.01) |
| B01J 23/46 | (2006.01) |
| C07C 15/14 | (2006.01) |
| C07C 5/42 | (2006.01) |
| B01J 35/00 | (2006.01) |
| B01J 21/04 | (2006.01) |
| B01J 27/26 | (2006.01) |
| C01B 3/22 | (2006.01) |

(52) U.S. Cl.
CPC .......... *B01J 27/26* (2013.01); *B01J 35/0006* (2013.01); *C01B 3/0015* (2013.01); *C01B 3/0078* (2013.01); *C01B 3/22* (2013.01); *C07C 5/42* (2013.01); *C07C 15/14* (2013.01); *C07C 15/16* (2013.01); *B01J 2231/64* (2013.01); *B01J 2231/70* (2013.01); *C01B 2203/0277* (2013.01); *C01B 2203/065* (2013.01); *C01B 2203/1064* (2013.01); *Y02E 60/327* (2013.01)

(56) References Cited

U.S. PATENT DOCUMENTS

| | | | |
|---|---|---|---|
| 8,563,465 B2 | 10/2013 | Nishihara et al. | |
| 2004/0223907 A1* | 11/2004 | Pez | C01B 3/0015 423/648.1 |
| 2009/0246575 A1 | 10/2009 | Zhao et al. | |
| 2010/0036145 A1 | 2/2010 | Kim et al. | |
| 2011/0171119 A1* | 7/2011 | Yazami | C01B 3/0015 423/657 |
| 2015/0266731 A1* | 9/2015 | Boesmann | C01B 3/0015 423/651 |
| 2017/0166496 A1* | 6/2017 | Imagawa | C01B 3/0015 |

FOREIGN PATENT DOCUMENTS

| | | |
|---|---|---|
| JP | 2009242232 A | 10/2009 |
| KR | 1020100019653 A | 2/2010 |
| KR | 1020150097558 A | 8/2015 |

OTHER PUBLICATIONS

Leonid M. Kustov et al., "Hydrogen storage materials", ScienceDirect, Mendeleev Communications, 2014, pp. 1-8, vol. 24.

Linlin Li et al., "Hydrogen storage and release from a new promising Liquid Organic Hydrogen Storage Carrier (LOHC): 2-methylindole", International Journal of Hydrogen Energy, May 24, 2016, pp. 16129-16134, vol. 41, Elsevier Ltd.

Michael G. Manas et al., "Iridium catalyzed reversible dehydrogenation—Hydrogenation of quinoline derivatives under mild conditions", Journal of Organometallic Chemistry, Apr. 23, 2015, pp. 184-189, vol. 792, Elsevier B.V.

Nicole Bruckner et al., "Evaluation of Industrially Applied Heat-Transfer Fluids as Liquid Organic Hydrogen Carrier Systems", ChemSusChem, 2014, pp. 229-235, vol. 7, Wiley-VCH Verlag GmbH & Co.

* cited by examiner ated under 35 U.S.C. § 119, the contents of which in its entirety are herein incorporated by reference.

LIQUID HYDROGEN STORAGE MATERIAL AND METHOD OF STORING HYDROGEN USING THE SAME

CROSS-REFERENCE TO RELATED APPLICATION

This application claims the priority of Korean Patent Application No. 10-2016-0126557, filed on Sep. 30, 2016, and all the benefits accruing therefrom under 35 U.S.C. § 119, the contents of which in its entirety are herein incorporated by reference.

BACKGROUND

1. Field

The present disclosure relates to a liquid hydrogen storage material and a method of storing hydrogen using the same.

DESCRIPTION OF THE NATIONAL SUPPORT RESEARCH AND DEVELOPMENT

This study is made by the support of the Korea Institute of Energy Technology Evaluation and Planning funded by the Ministry of Trade, Industry and Energy, Republic of Korea under the supervision of Korea Institute of Science and Technology, the project title is 'Development of New Renewable Energy Core Technology, and the project name is 'Development of 0.5 kWh-class liquid biphenyl/carbazole-based reversible hydrogen storage system' (Project identification No.: 1415143655).

2. Description of the Related Art

Due to the depletion of fossil fuels and environmental pollution problems, the demand for new renewable alternative energy is high, and hydrogen has drawn attention as an alternative energy to fossil fuels. In particular, in the case of fuel cell and hydrogen combustion devices, hydrogen is used as an energy carrier, and in order to apply the fuel cell and/or hydrogen combustion devices to, for example, automobiles, stationary applications, or various electronic products, and the like, there is a need for a safe and sustainable technology for storing and supplying hydrogen.

In a device that uses hydrogen, it is possible to use a system in which hydrogen is supplied, whenever hydrogen is needed, from a hydrogen storage device (hydrogen supply device) installed separately to supply hydrogen. Representative examples thereof include compressed hydrogen storage and liquefied hydrogen storage methods, and these technologies may have an issue of price and safety in transporting hydrogen from where hydrogen is produced to where hydrogen is needed.

Besides, it is possible to use a system in which hydrogen is generated by mounting a material that stores and generates hydrogen in a device that uses hydrogen to react the corresponding material, and the hydrogen is supplied. In the system, a method of using metal hydride, a method of using absorbents/carbon, a chemical hydrogen storage method, and the like have been proposed, and a hydrogen storage technology using various chemical hydrides such as ammonia borane, silane compounds, and formic acid has been studied.

In addition, recently, a hydrogen storage technology using an easily reversible organic compound has been actively studied, and for example, in Japan, a hydrogen power plant connected with a hydrogen storage technology based on toluene/methylcyclohexane has been established in consideration of an economical hydrogen transportation, and in Germany, there have been attempts to reveal reversible hydrogen storage characteristics based on dibenzyl toluene-based compounds. However, in Korea, aromatic ring compound-based compounds which enable hydrogen to be reversibly stored and released has been little explored.

REFERENCES OF THE RELATED ART

Non-Patent Documents (Non-Patent Document 1) Stark, Katharina, et al. "Melting Points of Potential Liquid Organic Hydrogen Carrier Systems Consisting of N-Alkylcarbazoles." Journal of Chemical & Engineering Data 61.4 (2016): 1441-1448.
(Non-Patent Document 2) Bruckner, N., et al. (2014). "Evaluation of industrially applied heat-transfer fluids as liquid organic hydrogen carrier systems." ChemSusChem 7(1): 229-235
(Non-Patent Document 3) Li, L., et al. (2016). "Hydrogen storage and release from a new promising Liquid Organic Hydrogen Storage Carrier (LOHC): 2-methylindole." International Journal of Hydrogen Energy.
(Non-Patent Document 4) Manas, M. G., et al. (2015). "Iridium catalyzed reversible dehydrogenation—Hydrogenation of quinoline derivatives under mild conditions." Journal of Organometallic Chemistry 792: 184-189.

SUMMARY

In an aspect, the present disclosure is directed to providing a liquid hydrogen storage material which not only exhibits a high hydrogen storage capacity, but also has an excellent price competitiveness.

In another aspect, the present disclosure is directed to providing a method of storing hydrogen using the liquid hydrogen storage material.

In an aspect, the present disclosure provides a liquid hydrogen storage material including 1,1'-biphenyl and 1,1'-methylenedibenzene, the liquid hydrogen storage material including the 1,1'-biphenyl and the 1,1'-methylenedibenzene at a weight ratio of 1:1 to 1:2.5.

In an exemplary embodiment, the liquid hydrogen storage material may include the 1,1'-biphenyl and the 1,1'-methylenedibenzene at a weight ratio of 1:1.8 to 1:2.5.

In an exemplary embodiment, the liquid hydrogen storage material may include the 1,1'-biphenyl and the 1,1'-methylenedibenzene at a weight ratio of 1:1.8.

In another exemplary embodiment, the 1,1'-biphenyl may be completely dissolved in the 1,1'-methylenedibenzene in order to form a liquid eutectic mixture.

In another aspect, the present disclosure provides a method of preparing a liquid hydrogen storage material, which prepares a liquid hydrogen storage material by dissolving a 1,1'-biphenyl solid in a 1,1'-methylenedibenzene liquid at a weight ratio of 1:1 to 1:2.5.

In an exemplary embodiment, the 1,1'-biphenyl solid may be dissolved in a 1,1'-methylenedibenzene liquid at a weight ratio of 1:1.8 to 1:2.5

In an exemplary embodiment, the 1,1'-biphenyl solid may be completely dissolved in the 1,1'-methylenedibenzene liquid to form a liquid eutectic mixture.

In still another aspect, the present disclosure provides a method of storing and releasing hydrogen, the method comprising: preparing a liquid hydrogen storage material by mixing 1,1'-biphenyl and 1,1'-methylenedibenzene at a weight ratio of 1:1 to 1:2.5; storing hydrogen by performing a hydrogenation reaction on the liquid hydrogen storage material; and releasing hydrogen by performing a dehydrogenation reaction on the liquid hydrogen storage material which has undergone the hydrogen generation reaction, after performing a hydrogenation reaction under a catalytic condition.

In an exemplary embodiment, the liquid hydrogen storage material comprises the 1,1'-biphenyl and the 1,1'-methylenedibenzene at a weight ratio of 1:1.8 to 1:2.5

In an exemplary embodiment, the hydrogenation reaction may be performed at a temperature condition of 80° C. to 150° C. under a pressure condition of 10 bar to 50 bar, preferably 40 to 50 bar.

In another exemplary embodiment, the hydrogenation reaction may be performed under a catalytic condition including ruthenium.

In another exemplary embodiment, the catalyst may be included at a weight ratio of 0.5 wt % to 7 wt % based on a total weight of the liquid hydrogen storage material.

In another exemplary embodiment, the dehydrogenation reaction is performed under a catalytic condition comprising palladium.

A liquid hydrogen storage material according to an aspect of the present disclosure may provide a hydrogen storage material for a fuel cell, which has not only a high hydrogen storage capacity, but also an excellent price competitiveness. Also, the hydrogen storage material can be used in all areas that need "hydrogen". For example, the hydrogen storage materials can be widely used in a variety of industries, including the petroleum industry (refining industry), chemical industry, metal industry, glass industry, food industry, electronics, etc.

According to a method of storing hydrogen according to an aspect of the present disclosure, the liquid hydrogen storage material can have a much higher hydrogen storage capacity per weight and volume than that of compressed gas, and can be easily stored and transported because the material is prepared in a liquid state. Accordingly, a method of storing hydrogen using the same can store hydrogen more economically because unnecessary initial investment costs may not be generated.

DETAILED DESCRIPTION

Hereinafter, embodiments of the present disclosure will be described in detail with reference to accompanying drawings. Embodiments of the present disclosure have been described with reference to accompanying drawings, but have been described for illustration, and the technical spirit of the present disclosure and the configuration and application thereof are not limited thereby.

The term "liquid" as used herein refers to a liquid state.

The term "hydrogen storage material" as used herein refers to a material which is reacted with a material including a hydrogen (H) atom to store the hydrogen atom through a chemical bond, and can reversibly release hydrogen ($H_2$) when a predetermined energy is applied thereto.

In an aspect, the present disclosure provides a liquid hydrogen storage material including 1,1'-biphenyl and 1,1'-methylenedibenzene, the liquid hydrogen storage material including the 1,1'-biphenyl and the 1,1'-methylenedibenzene at a weight ratio of 1:1 to 1:2.5.

The liquid hydrogen storage material may be prepared by mixing a 1,1'-biphenyl solid and a 1,1'-methylenedibenzene liquid at a weight ratio of 1:1 to 1:2.5 to dissolve the 1,1'-biphenyl solid in the 1,1'-methylenedibenzene liquid. Particularly, 1,1'-biphenyl solid and a 1,1'-methylenedibenzene liquid can be mixed at a weight ratio of 1:1.8 to 1:2.5 to completely dissolve the 1,1'-biphenyl solid in the 1,1'-methylenedibenzene liquid. That is, in the liquid hydrogen storage material, the 1,1'-biphenyl solid may be completely dissolved and liquefied in the 1,1'-methylenedibenzene liquid to form a liquid eutectic mixture.

In an exemplary embodiment, the liquid hydrogen storage material may include the 1,1'-biphenyl and the 1,1'-methylenedibenzene at a weight ratio of 1:1.8.

Accordingly, the liquid hydrogen storage material can have a much higher hydrogen storage capacity per weight and volume than that of compressed gas, and can be easily stored and transported because the material is prepared in a liquid state. Accordingly, for example, when a fuel cell which uses the same is manufactured, hydrogen can be stored more economically because unnecessary initial investment costs may not be generated.

Hereinafter, the present disclosure will be examined in detail.

Figure 1:
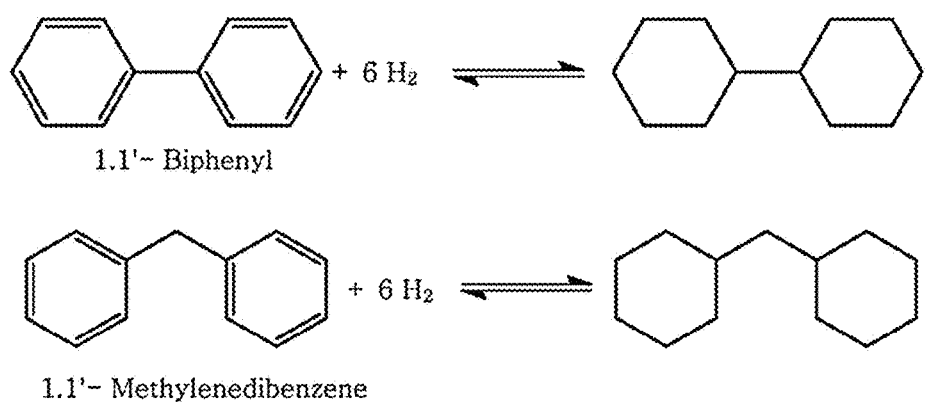
FIG. 1 is a schematic view illustrating a hydrogenation reaction of 1,1'-biphenyl and 1,1'-methylenedibenzene.

In an exemplary embodiment, the 1,1'-biphenyl and the 1,1'-methylenedibenzene have a plurality of double bonds in the molecule, and thus easily store hydrogen (see FIG. 1). 1,1'-biphenyl has a hydrogen storage capacity of 7.2 wt % based on the weight of 100% 1,1'-biphenyl, and 1,1'-methylenedibenzene has a hydrogen storage capacity of 6.7 wt % based on the weight of 100% 1,1'-methylenedibenzene.

Figure 2A:
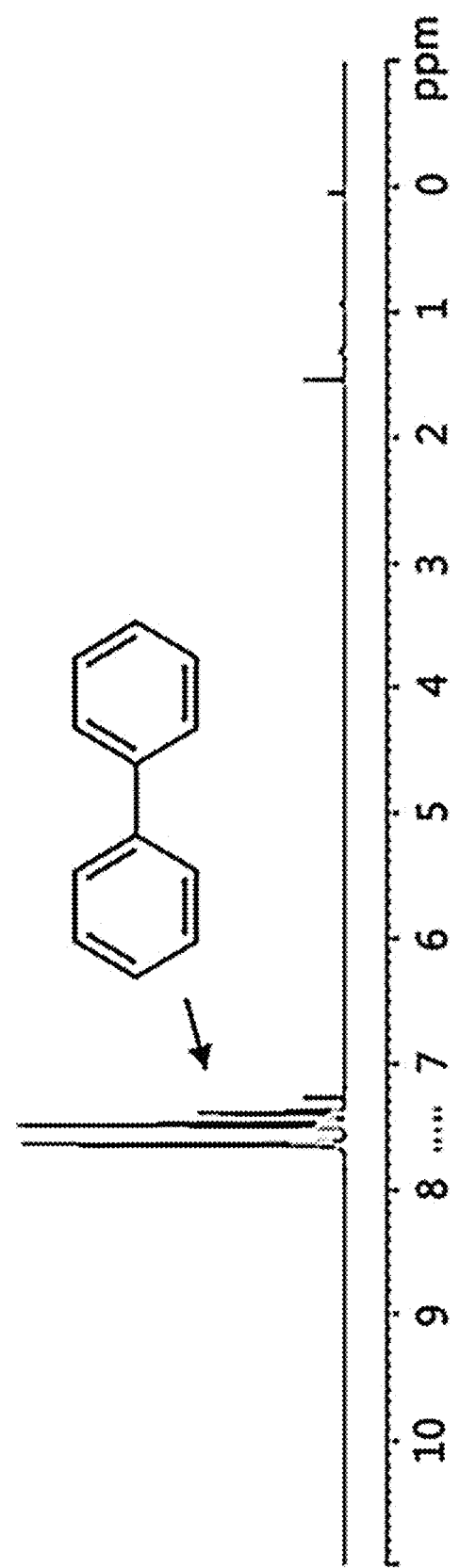
FIGS. 2A and 2B illustrate $^1$H-NMR spectrum results of 1,1'-biphenyl before (FIG. 2A) and after (FIG. 2B) the hydrogenation reaction.
Figure 2B:
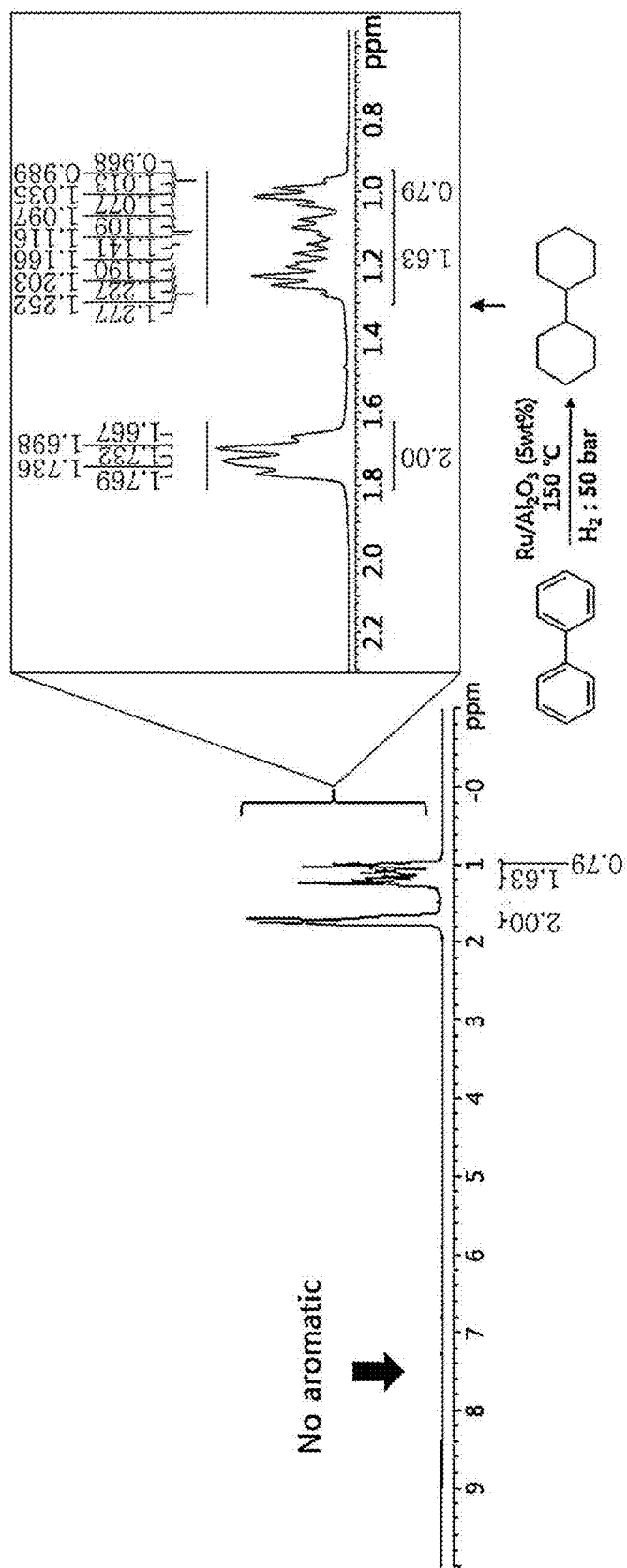

Specifically, when 1,1'-biphenyl is described by taking an example, it can be confirmed that when a hydrogenation reaction of 1,1'-biphenyl is performed, the $^1$H-NMR peak corresponding to proton disposed in the benzene ring in the 1,1'-biphenyl disappears simultaneously with the hydrogenation reaction, and the $^1$H-NMR spectrum shifts. FIGS. 2A and 2B illustrate $^1$H-NMR spectrum results of 1,1,'-biphenyl before (FIG. 2A) and after (FIG. 2B) the hydrogenation reaction, and when these results are compared with each other, it can be confirmed that when a hydrogenation reaction of 1,1'-biphenyl is performed, the $^1$H-NMR peak corresponding to proton disposed in the benzene ring in the 1,1'-biphenyl disappears simultaneously with the hydrogenation reaction, and the $^1$H-NMR spectrum shifts.

Meanwhile, the liquid hydrogen storage material of the present disclosure may include 1,1'-biphenyl and 1,1'-methylenedibenzene at a weight ratio of 1:1 to 1:2.5, and may preferably include 1,1'-biphenyl and 1,1'-methylenedibenzene at a weight ratio of 1:1.8 to 1:2.5.

In an exemplary embodiment, the liquid hydrogen storage material may include the 1,1'-biphenyl and the 1,1'-methylenedibenzene at a weight ratio of 1:1.8.

In an exemplary embodiment, when 1,1'-biphenyl and 1,1'-methylenedibenzene are included at a weight ratio of less than 1:1, it may be difficult to implement a liquid hydrogen storage material because 1,1'-biphenyl is not dissolved in 1,1'-methylenedibenzene. In contrast, when the weight ratio of 1,1'-biphenyl and 1,1'-methylenedibenzene exceeds 1:2.5, the liquid hydrogen storage material may not have a price competitiveness because the relatively expensive 1,1'-methylenedibenzene is excessively included. In addition, since the range is an optimized range in which 1,1'-biphenyl may be dissolved, the amount of 1,1'-biphenyl used may be maximized, and as a result, the hydrogen storage capacity may be finally maximized.

In another aspect, the present disclosure provides a method of preparing a liquid hydrogen storage material, which prepares a liquid hydrogen storage material by mixing a 1,1'-biphenyl solid in a 1,1'-methylenedibenzene liquid at a weight ratio of 1:1 to 1:2.5, as described above. As described above, even when the 1,1'-biphenyl solid and the 1,1'-methylenedibenzene liquid are only mixed at a ratio within a predetermined range, the 1,1'-biphenyl solid may be dissolved in the 1,1'-methylenedibenzene liquid.

Particularly, the liquid hydrogen storage material may include the 1,1'-biphenyl and the 1,1'-methylenedibenzene at a weight ratio of 1:1.8 to 1:2.5. Even when the 1,1'-biphenyl solid and the 1,1'-methylenedibenzene liquid are only mixed at a ratio within a predetermined range, the 1,1'-biphenyl solid may be completely dissolved in the 1,1'-methylenedibenzene liquid.

In an exemplary embodiment, the mixing process may be performed within a temperature range of −15° C. to 100° C., and may be performed, for example, under a condition of 1 atm at room temperature. When the mixing temperature is below than −15° C., the mixture is solidified, and as a result, the two materials may not be easily mixed, and when the mixing temperature is over than 100° C., a portion of the compounds constituting the mixture may be evaporated.

Meanwhile, in still another aspect, the present disclosure provides a method of storing and releasing hydrogen, the method including: preparing a liquid hydrogen storage material by mixing a 1,1'-biphenyl solid and a 1,1'-methylenedibenzene liquid at a weight ratio of 1:1 to 1:2.5; and storing hydrogen by performing a hydrogenation reaction on the liquid hydrogen storage material; and releasing hydrogen by performing a dehydrogenation reaction on the liquid hydrogen storage material which has undergone the hydrogen generation reaction, after performing a hydrogenation reaction under a catalytic condition. Meanwhile, since the hydrogen storage method includes a configuration which is substantially same as or similar to the above-described method of preparing a liquid hydrogen storage material, the description thereof will be omitted.

In an exemplary embodiment, the liquid hydrogen storage material may include the 1,1'-biphenyl and the 1,1'-methylenedibenzene at a weight ratio of 1:1 to 1:2.5.

The hydrogen storage method includes performing a hydrogenation reaction on the above-described liquid hydrogen storage material. In this case, a hydrogen ($H_2$) gas as a reaction gas may be injected into a reactor.

In an exemplary embodiment, the hydrogenation reaction may be performed at a temperature condition of 80° C. to 150° C. under a pressure condition of 10 bar to 50 bar, preferably 40 bar to 50 bar.

When the temperature of the hydrogenation reaction is less than the range, the hydrogenation reaction rate may be reduced, and when the temperature exceeds the range, the compounds may be decomposed.

Meanwhile, a chamber in which the hydrogenation reaction is performed may have a pressure within a range of 10 bar to 300 bar (or 40 bar to 300 bar), and when the pressure condition is less than the range, the hydrogenation reaction rate may be reduced, and when the pressure exceeds the range, the economic efficiency of manufacturing a reactor may deteriorate.

Meanwhile, when the hydrogenation reaction is performed, a catalyst may be used in order to perform a hydrogenation reaction more smoothly.

In an aspect, the catalyst may be a ruthenium-based catalyst, that is, a catalyst including ruthenium. Specifically, the catalyst may be a ruthenium catalyst immobilized on various metal oxides such as $Ru/Al_2O_3$, $Ru/ZrO_2$, and $Ru/CeO_2$, and may include one or more selected from the group consisting of ruthenium catalysts immobilized on a carbon-based support, such as Ru/C, Ru/carbon nanotubes, and Ru/graphene.

In an exemplary embodiment, the catalyst may be included at a weight ratio of 0.5 wt % to 7 wt % based on a total weight of the liquid hydrogen storage material, and may be included at a weight ratio of preferably 5 wt % to 7 wt %. When the catalyst is included at a weight ratio of less than 0.5 wt %, the catalyst may not significantly contribute to the hydrogenation reaction, and when the catalyst is reacted at a weight ratio of more than 7 wt %, costs required for the preparation process may be increased because an unnecessarily large amount of catalyst is used.

In an exemplary embodiment, the dehydrogenation reaction is performed under the catalytic condition comprising palladium.

In another aspect, the catalyst may be a palladium-based catalyst, that is, a catalyst including palladium.

In an exemplary embodiment, when the liquid hydrogen storage material is used, the hydrogen storage rate may be greatly excellent because 1,1'-biphenyl and 1,1'-methylenedibenzne, which each have excellent hydrogen storage capacity, are used in a liquid state.

For example, the liquid hydrogen storage material may store hydrogen in an amount of 5 wt % or more based on a total weight of the liquid hydrogen storage material, and may store hydrogen in an amount of 55 $gH_2/L$ or more based on a total volume of the liquid hydrogen storage material.

In addition, since the liquid hydrogen storage material is used, it is possible to minimize costs required for storing and transporting a hydrogen storage material, and as a result, it is possible to minimize costs required for storing hydrogen. Accordingly, a final product such as fuel cell may be manufactured so as to have a price competitiveness.

Hereinafter, the present disclosure will be described in more detail through Examples. These Examples are only for exemplifying the present disclosure, and it will be obvious to those skilled in the art that the scope of the present disclosure is not interpreted to be limited by these Examples.

Experimental Example 1

A hydrogen storage material was prepared by mixing 1,1'-biphenyl and 1,1'-methylenedibenzene at a ratio shown in the following Table 1. In this case, the temperature was 25° C., the pressure was 1 atm, and the mixing reaction was performed within 60 minutes.

TABLE 1

| Liquid hydrogen storage material | 1,1'-biphenyl | 1,1'-methylene-dibenzene | Degree of liquefaction |
|---|---|---|---|
| Example 1 | 1.0 g | 2.3 g | Completely liquefied |
| Example 2 | 1.0 g | 1.8 g | Completely liquefied |
| Comparative Example 1 | 1.0 g | 1.5 g | Partially liquefied (a small amount thereof was crystallized) |
| Comparative Example 2 | 1.0 g | 1.0 g | Partially liquefied (a large amount thereof was crystallized) |

Figure 3A:
FIGS. 3A and 3B are a photograph illustrating the solubility of the liquid hydrogen storage materials prepared according to Examples 1 and 2.
Figure 3B:
Figure 4A:
FIGS. 4A and 4B are a photograph illustrating the solubility of the liquid hydrogen storage materials prepared according to Comparative Examples 1 and 2.
Figure 4B:

A reaction vessel including the hydrogen storage materials prepared according to Examples 1 and 2 and Comparative Examples 1 and 2 was observed by the unaided eye and photographed, and the photographs are illustrated in FIGS. 3A to 4B. FIGS. 3A and 3B are a photograph illustrating the solubility of the hydrogen storage materials prepared according to Examples 1 and 2, and FIGS. 4A and 4B are a photograph illustrating the solubility of the hydrogen storage materials prepared according to Comparative Examples 1 and 2.

When FIGS. 3A to 4B were examined, it could be confirmed that in the hydrogen storage materials prepared according to Examples 1 and 2, a liquid hydrogen storage material was implemented because 1,1'-biphenyl was completely dissolved in 1,1'-methylenedibenzene. In contrast, when the hydrogen storage materials prepared in Comparative Examples 1 and 2 were examined, it could be confirmed that crystals were produced while 1,1'-biphenyl was not completely dissolved in 1,1'-methylenedibenzene. In particular, when 1,1'-methylenedibenzene and 1,1'-biphenyl were reacted at a ratio of 1:1, it could be confirmed that a large amount of crystals of 1,1'-biphenyl was precipitated.

Experimental Example 2

A liquid hydrogen storage material was prepared by mixing 1,1'-biphenyl and 1,1'-methylenedibenzene at a ratio (1.85 wt %) shown in the following Table 2.

TABLE 2

| | 1,1'-biphenyl | 1,1'-methylene-dibenzene | Catalyst | Temperature | Pressure ($H_2$) |
|---|---|---|---|---|---|
| Example 4 | 2 g | 3.7 g | $Ru/Al_2O_3$ (5 wt %) | 150° C. | 50 bar |
| Example 5 | 2 g | 3.7 g | $Ru/Al_2O_3$ (5 wt %) | 100° C. | 50 bar |
| Example 6 | 2 g | 3.7 g | $Ru/Al_2O_3$ (5 wt %) | 80° C. | 50 bar |
| Example 7 | 2 g | 3.7 g | $Ru/Al_2O_3$ (5 wt %) | 150° C. | 40 bar |
| Example 8 | 2 g | 3.7 g | $Ru/Al_2O_3$ (5 wt %) | 100° C. | 40 bar |
| Example 9 | 2 g | 3.7 g | $Ru/Al_2O_3$ (5 wt %) | 80° C. | 40 bar |

Thereafter, under the temperature, pressure, and catalytic conditions shown in Table 3, the hydrogenation reaction was performed by reacting the chamber including each of the liquid hydrogen storage materials with a hydrogen ($H_2$) gas.

Figure 5A:
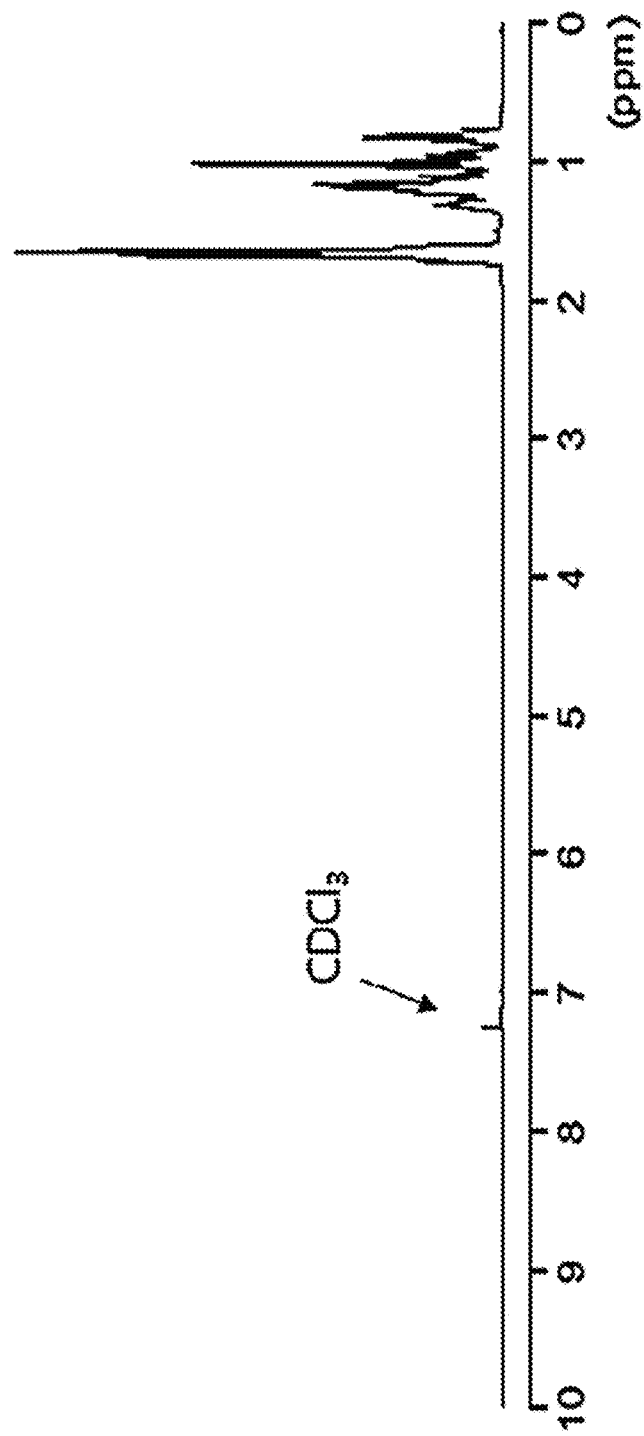
FIG. 5A is a graph illustrating $^1$H-NMR spectrum results determined after a hydrogenation reaction is performed by using the liquid hydrogen storage material according to an aspect of the present disclosure.
Figure 5B:
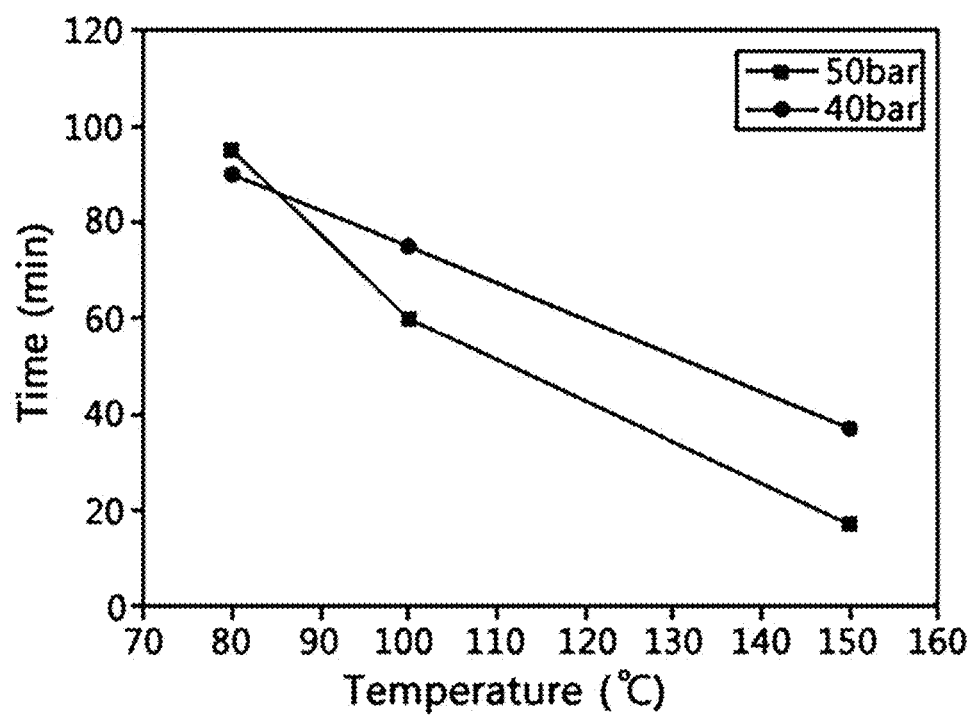
FIG. 5B is a graph illustrating the reaction completion time in the case where a hydrogenation reaction is performed under predetermined pressure and temperature conditions by using the liquid hydrogen storage material according to an aspect of the present disclosure.
Figure 6:
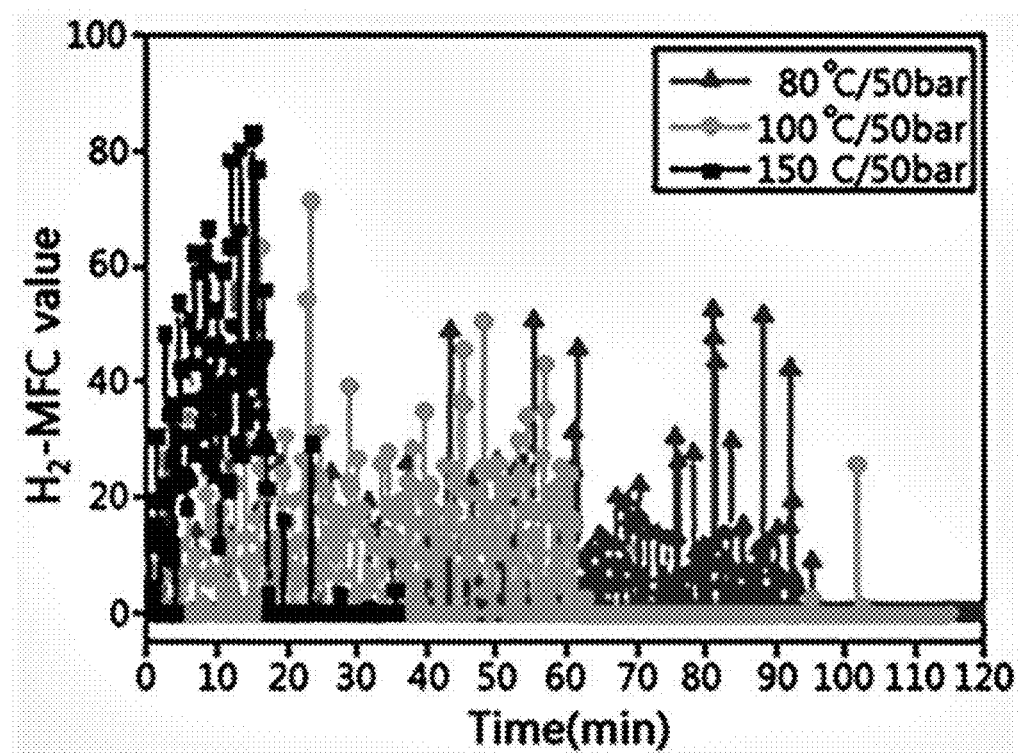
FIG. 6 is a graph illustrating MFC values of the liquid hydrogen storage material according to an aspect of the present disclosure under a different temperature condition under a condition of 50 bar.
Figure 7:
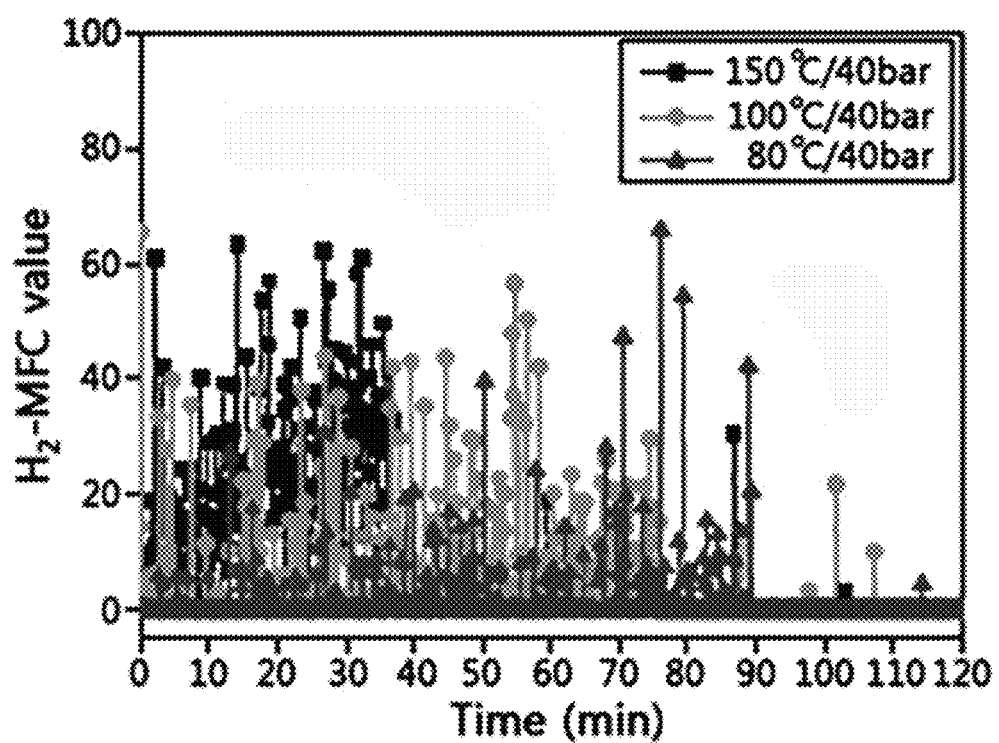
FIG. 7 is a graph illustrating MFC values of the liquid hydrogen storage material according to an aspect of the present disclosure under a different temperature condition under a condition of 40 bar.

Subsequently, the $^1$H-NMR spectrum results of the final products are illustrated in FIG. 5A, the time taken for the hydrogenation reaction according to the change in high temperature and pressure was measured, and is illustrated in FIG. 5B, and the time taken for the reaction in each Example is shown in Table 3. Further, under fixed pressure conditions of 50 bar and 40 bar, the MFC value over each time was measured, and is illustrated in FIGS. 6 and 7. In the tables and the drawings, the time taken for the reaction means a reaction completion time in which the hydrogen storage material and the hydrogen ($H_2$) gas to be injected are not reacted with each other any more.

TABLE 3

| | 1,1'-biphenyl | 1,1'-methylene-dibenzene | Time taken for reaction |
|---|---|---|---|
| Example 4 | 2 g | 3.7 g | 17 minutes |
| Example 5 | 2 g | 3.7 g | 60 minutes |
| Example 6 | 2 g | 3.7 g | 95 minutes |
| Example 7 | 2 g | 3.7 g | 37 minutes |
| Example 8 | 2 g | 3.7 g | 75 minutes |
| Example 9 | 2 g | 3.7 g | 90 minutes |

When FIG. 5 was examined, it could be confirmed that the hydrogenation reaction properly proceeded because a portion corresponding to the benzene ring in the $^1$H-NMR spectrum was not discovered. In addition, when Table 3 and FIGS. 5A, 6, and 7 were examined, it could be confirmed that the reaction was most smoothly performed under the conditions of 150° C. and 50 bar.

Experimental Example 3

A liquid hydrogen storage material was prepared by mixing 1,1'-biphenyl and 1,1'-methylenedibenzene at a ratio (1.85 wt %) shown in the following Table 4, and the hydrogenation reaction was performed by reacting a chamber including each hydrogen storage material with a hydrogen ($H_2$) gas under the conditions of a temperature of 150° C. and a pressure of 50 bar and under the catalytic conditions shown in Table 4.

Figure 8:
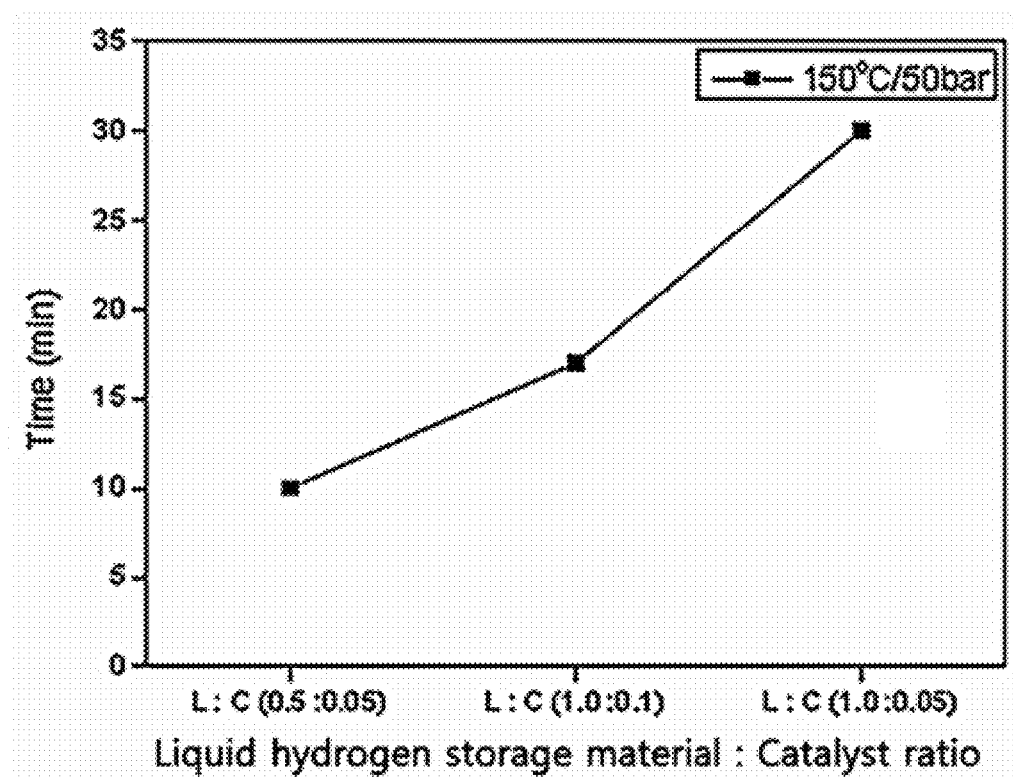
FIG. 8 is a graph illustrating a hydrogenation reaction time according to the ratio of a mixture of 1,1'-biphenyl and 1,1'-methylenedibenzene and a catalyst in a liquid hydrogen storage material.
Figure 9:
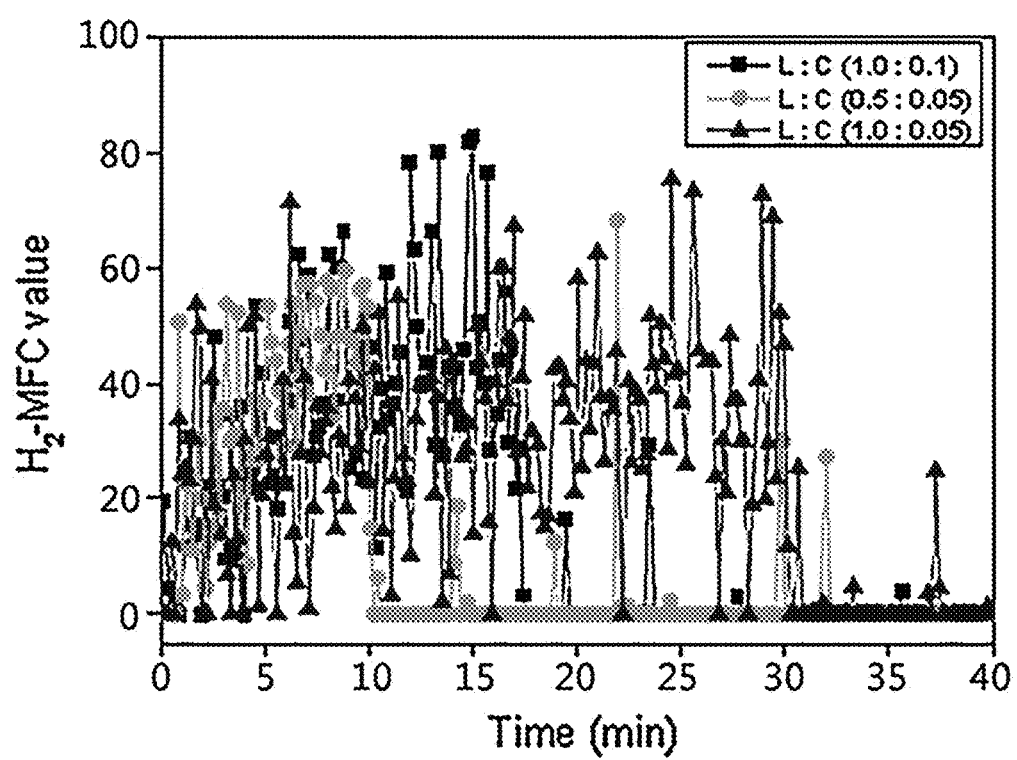
FIG. 9 is a graph illustrating MFC values according to each reaction time at a ratio of a mixture of 1,1'-biphenyl and 1,1'-methylenedibenzene and a catalyst in a liquid hydrogen storage material.

Thereafter, the time taken for the completion of the reaction of the final product was measured, and is shown in Table 4 and FIGS. 8 and 9.

TABLE 4

| | 1,1'-biphenyl | 1,1'-methylene-dibenzene | Catalyst | Weight ratio of liquid hydrogen storage material and catalyst | Time taken for reaction |
|---|---|---|---|---|---|
| Example 4 | 2 g | 3.7 g | $Ru/Al_2O_3$ (5 wt %) (0.57 g) | 1.0:0.1 | 17 minutes |
| Example 10 | 1 g | 1.85 g | $Ru/Al_2O_3$ (5 wt %) (0.285 g) | 0.5:0.05 | 10 minutes |
| Example 11 | 2 g | 3.7 g | $Ru/Al_2O_3$ (5 wt %) (0.285 g) | 1.0:0.05 | 30 minutes |

When Table 4 was examined, it could be confirmed that even when the content ratio of 1,1'-biphenyl, 1,1'-methylenedibenzene, and the catalyst was reduced to half the original value, the hydrogenation reaction was smoothly performed. In particular, in the case of Example 10, it could be confirmed that it took 10 minutes for the completion of the reaction.

Experimental Example 4

Figure 10:
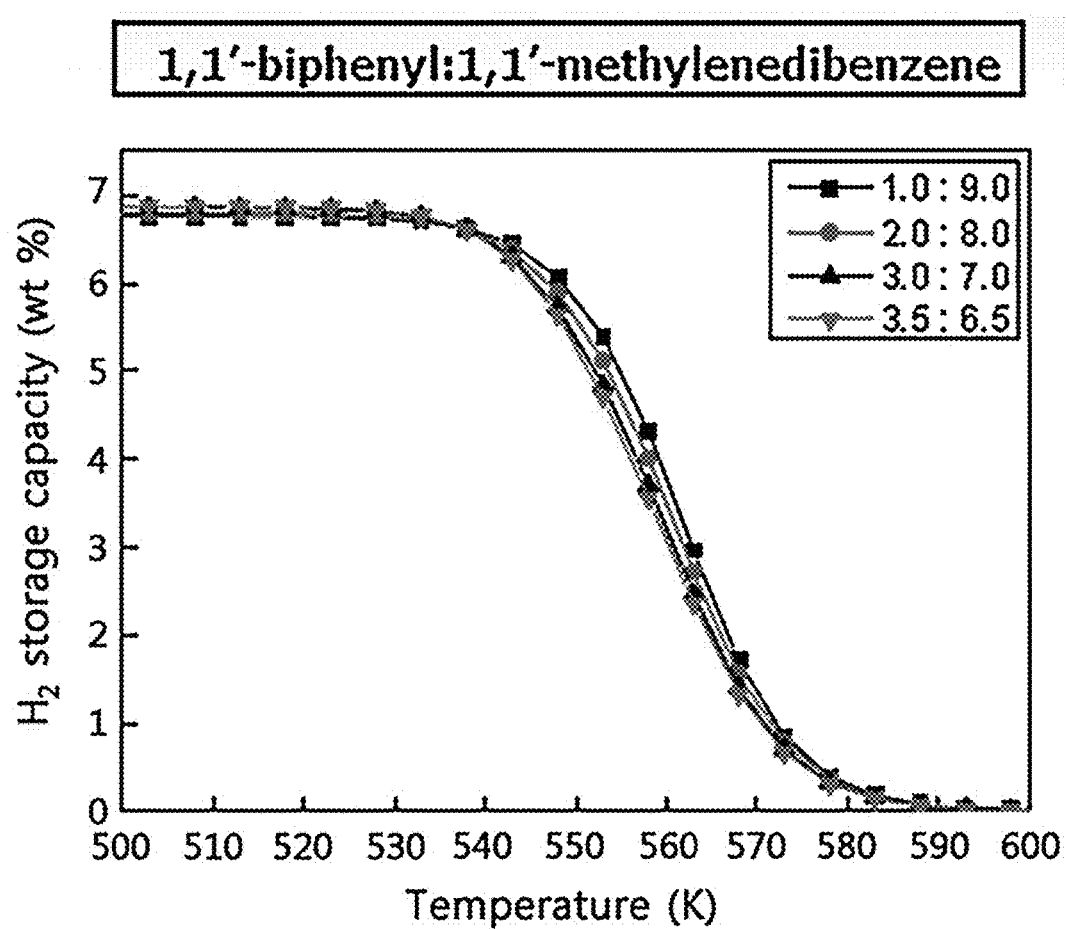
FIGS. 10 and 11 are a graph illustrating a hydrogen storage capacity over temperature according to the mixture ratio of 1,1'-biphenyl and 1,1'-methylenedibenzene in the liquid hydrogen storage material according to an aspect of the present disclosure.
Figure 11:
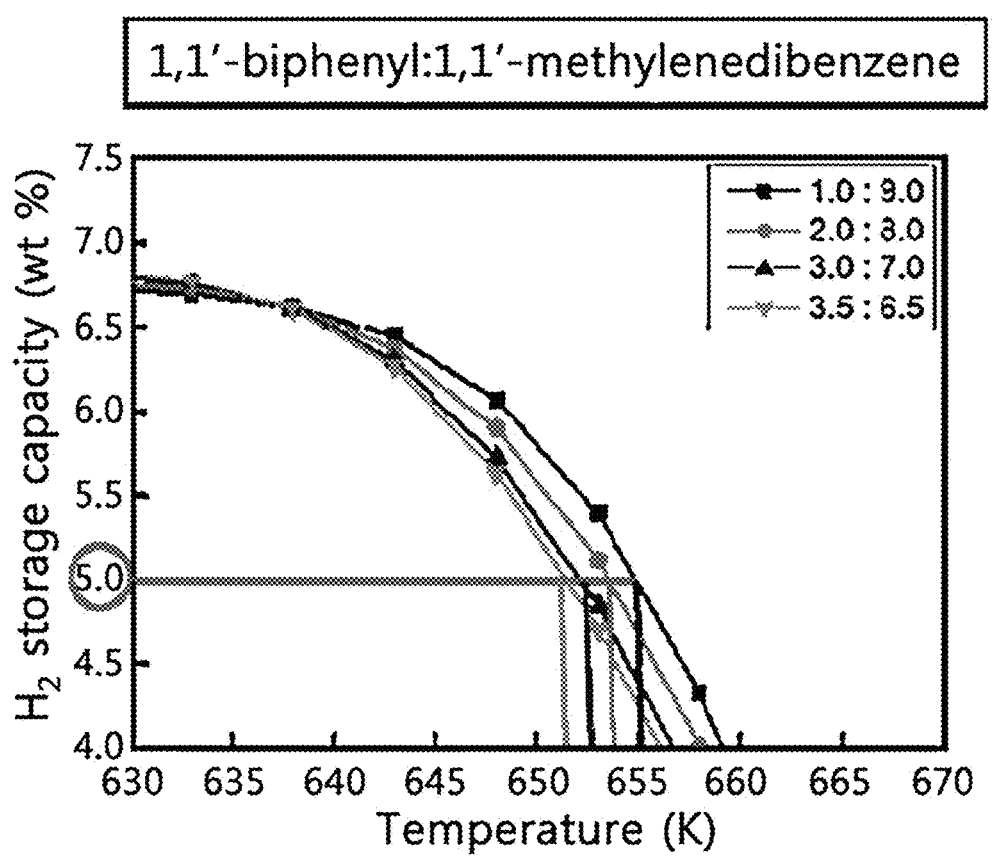

A liquid hydrogen storage material was prepared by mixing 1,1'-biphenyl and 1,1'-methylenedibenzene at the ratio shown in the following Table 5, and the hydrogen storage capacity for each temperature according to the equilibrium conversion data (liquid state) of each material was calculated and observed, and is illustrated in FIGS. 10 and 11.

TABLE 5

| | 1,1'-biphenyl | 1,1'-methylene-dibenzene |
|---|---|---|
| Example 12 | 3.0 g | 7.0 g |
| Example 13 | 3.5 g | 6.5 g |
| Comparative Example 3 | 1.0 g | 9.0 g |
| Comparative Example 4 | 2.0 g | 8.0 g |

When FIGS. 10 and 11 were examined, it could be confirmed that in a range of 500 K to 600 K, a hydrogen storage capacity value of about 0.01 wt % to about 7 wt % was exhibited based on a total weight of the liquid hydrogen storage material, and in particular, in the case of the liquid hydrogen storage materials according to Examples 12 and 13, it could be confirmed that under a temperature condition of about 551 K to about 554 K, a hydrogen storage capacity value of about 5 wt % was exhibited.

Experimental Example 5

A liquid hydrogen storage material was prepared by mixing 1,1'-biphenyl and 1,1'-methylenedibenzene according to Example 1, and the hydrogenation reaction was performed by reacting the liquid hydrogen storage material with a hydrogen ($H_2$) gas in a chamber including each of the hydrogen storage materials under the conditions of a temperature of 150° C. and a pressure of 50 bar and under a catalytic condition of $Ru/Al_2O_3$ (5 wt %).

Figure 12:
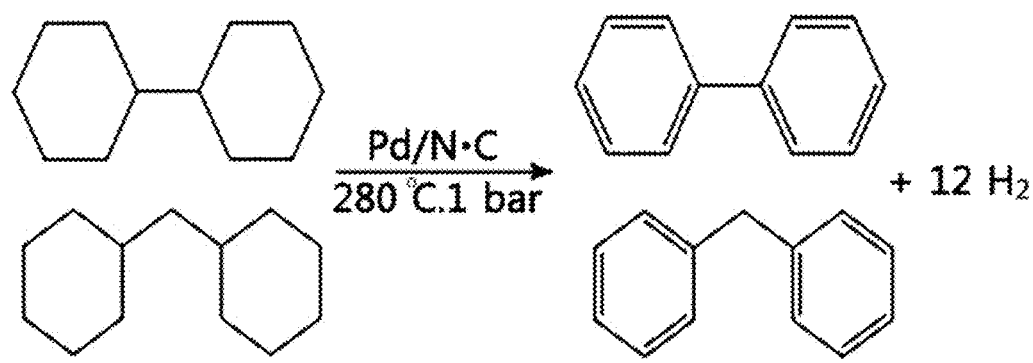
FIG. 12 illustrates a reaction schematic view of the case where a dehydrogenation reaction is performed when hydrogen is stored by using the liquid hydrogen storage material according to an aspect of the present disclosure.

Thereafter, under a temperature condition of 280° C., a pressure condition of 1 bar, and a catalytic condition of Pd/N—C (8 wt %), a dehydrogenation reaction was performed by using the hydrogenated liquid hydrogen storage material under a catalytic condition comprising palladium (see FIG. 12).

Figure 13:
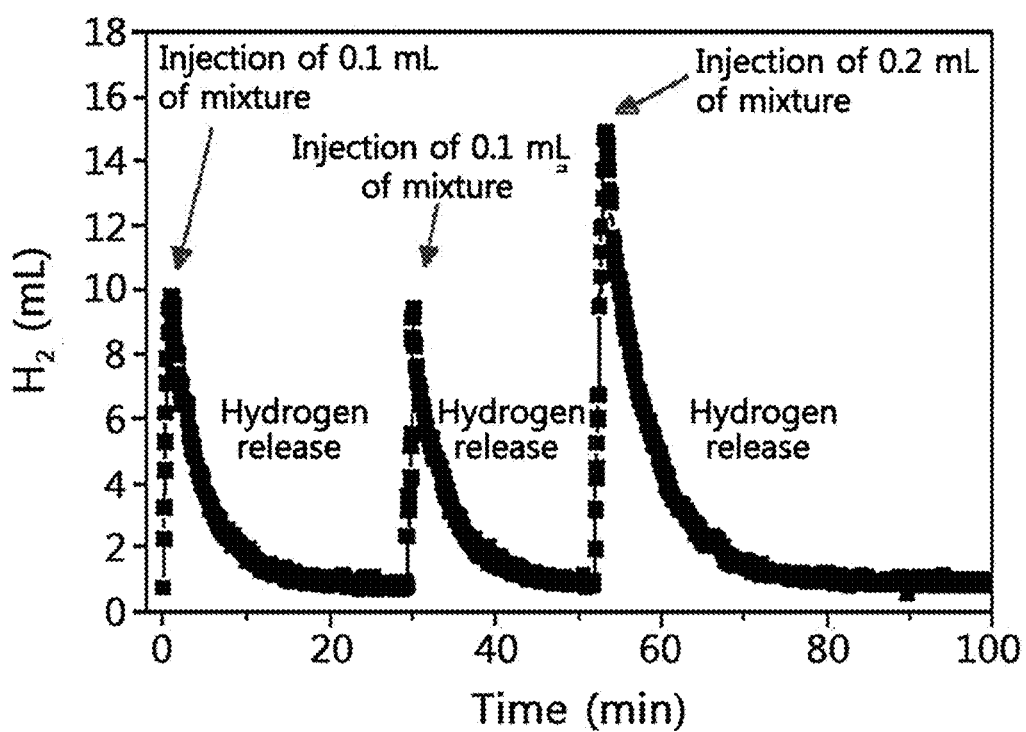
FIG. 13 is a graph illustrating an amount of hydrogen released in the case where a dehydrogenation reaction is performed when hydrogen is stored by using the liquid hydrogen storage material according to an aspect of the present disclosure.

When FIG. 13 was examined, it could be confirmed that when the hydrogenation reaction was performed by using the liquid hydrogen storage material prepared according to Example 1, and the dehydrogenation reaction was performed, hydrogen was released at a conversion rate of about 80% or more.

Accordingly, it could be confirmed that the liquid hydrogen storage material according to the present disclosure has a much higher hydrogen storage capacity per weight and volume than those of other compressed gases, and thus, can be widely used in the field which requires hydrogen to be stored and released.

The Examples of the present disclosure previously described should not be interpreted to limit the technical spirit of the present disclosure. The scope of the present disclosure to be protected is limited only by the matters described in the claims, and those skilled in the art of the present disclosure can improve and change the technical spirit of the present disclosure in various forms. Therefore, such improvements and changes would fall within the scope of the present disclosure to be protected as long as they are obvious to those skilled in the art.

What is claimed is:

1. A liquid hydrogen storage material comprising 1,1'-biphenyl and 1,1'-methylenedibenzene,
the liquid hydrogen storage material comprising the 1,1'-biphenyl and the 1,1'-methylenedibenzene at a weight ratio of 1:1 to 1:2.5.

2. The liquid hydrogen storage material according to claim 1, wherein the liquid hydrogen storage material comprises the 1,1'-biphenyl and the 1,1'-methylenedibenzene at a weight ratio of 1:1.8 to 1:2.5.

3. The liquid hydrogen storage material according to claim 2, wherein the liquid hydrogen storage material comprises the 1,1'-biphenyl and the 1,1'-methylenedibenzene at a weight ratio of 1:1.8.

4. The liquid hydrogen storage material according to claim 2, wherein the 1,1'-biphenyl is completely dissolved in the 1,1'-methylenedibenzene in order to form a liquid eutectic mixture.

5. A method of preparing a liquid hydrogen storage material, comprising preparing the liquid hydrogen storage material by dissolving a 1,1'-biphenyl solid in a 1,1'-methylenedibenzene liquid at a weight ratio of 1:1 to 1:2.5.

6. The method according to claim 5, wherein the liquid hydrogen storage material comprises the 1,1'-biphenyl and the 1,1'-methylenedibenzene at a weight ratio of 1:1.8 to 1:2.5.

7. The method according to claim 6, wherein the 1,1'-biphenyl solid is completely dissolved in the 1,1'-methylenedibenzene liquid in order to form a liquid eutectic mixture.

8. A method of storing and releasing hydrogen, the method comprising:

preparing a liquid hydrogen storage material by mixing 1,1'-biphenyl and 1,1'-methylenedibenzene at a weight ratio of 1:1 to 1:2.5;

storing hydrogen by performing a hydrogenation reaction on the liquid hydrogen storage material; and releasing hydrogen by performing a dehydrogenation reaction on the liquid hydrogen storage material which has undergone the hydrogen generation reaction, after performing a hydrogenation reaction under a catalytic condition.

9. The method according to claim 8, wherein the liquid hydrogen storage material comprises the 1,1'-biphenyl and the 1,1'-methylenedibenzene at a weight ratio of 1:1.8 to 1:2.5.

10. The method according to claim 8, wherein the hydrogenation reaction is performed at a temperature condition of 80° C. to 150° C. under a pressure condition of 10 bar to 50 bar.

11. The method according to claim 8, wherein the hydrogenation reaction is performed under a catalytic condition comprising ruthenium.

12. The method according to claim 11, wherein the catalyst is reacted at a weight ratio of 0.5 wt % to 7 wt % based on a total weight of the liquid hydrogen storage material.

13. The method according to claim 8, wherein the dehydrogenation reaction is performed under a catalytic condition comprising palladium.

* * * * *